(12) United States Patent
Kozaczek et al.

(10) Patent No.: US 6,792,075 B2
(45) Date of Patent: Sep. 14, 2004

(54) METHOD AND APPARATUS FOR THIN FILM THICKNESS MAPPING

(75) Inventors: Krzysztof J. Kozaczek, State College, PA (US); David S. Kurtz, State College, PA (US); Paul R. Moran, Port Matilda, PA (US); Roger I. Martin, State College, PA (US); Patrick W. Dehaven, Poughkeepsie, NY (US); Kenneth P. Rodbell, Sandy Hook, CT (US); Sandra G. Malhotra, Beacon, NY (US)

(73) Assignee: HyperNex, Inc., State College, PA (US)

( * ) Notice: Subject to any disclaimer, the term of this patent is extended or adjusted under 35 U.S.C. 154(b) by 37 days.

(21) Appl. No.: 10/225,534

(22) Filed: Aug. 21, 2002

(65) Prior Publication Data

US 2004/0047447 A1 Mar. 11, 2004

(51) Int. Cl.[7] .............................................. G01N 23/20
(52) U.S. Cl. .............................. 378/71; 378/73; 378/50
(58) Field of Search ............................. 378/71, 73, 79, 378/81, 89, 90, 50

(56) References Cited

U.S. PATENT DOCUMENTS

| | | | |
|---|---|---|---|
| 3,816,747 A | * 6/1974 | Kishino | 378/73 |
| 4,412,345 A | * 10/1983 | Workman et al. | 378/78 |
| 4,764,945 A | 8/1988 | Abe | 378/50 |
| 4,959,848 A | 9/1990 | Parobek | 378/46 |
| 5,003,569 A | 3/1991 | Okada et al. | 378/70 |
| 5,048,340 A | 9/1991 | Thompson et al. | 73/597 |
| 5,187,729 A | * 2/1993 | Ibe et al. | 378/73 |
| 5,414,747 A | * 5/1995 | Ruud et al. | 378/83 |
| 5,966,423 A | * 10/1999 | Quinn et al. | 378/81 |
| 6,005,914 A | * 12/1999 | Quinn et al. | 378/81 |
| 6,064,717 A | * 5/2000 | Ortega et al. | 378/71 |
| 6,226,349 B1 | * 5/2001 | Schuster et al. | 378/84 |
| 6,229,255 B1 | 5/2001 | Kim et al. | 313/402 |
| 6,301,330 B1 | * 10/2001 | Kurtz et al. | 378/71 |

OTHER PUBLICATIONS

I. Tomov et al., *Texture and Secondary Extinction Measurements in Al/Ti Stratified Films by X–Ray Diffraction*, Vacuum, vol. 50, No. 3, pp. 497–502 (1998).

J. Chaudhuri and F. Hashmi, *Determination of Thickness of Multiple Layer Thin Films by an X–Ray–Diffraction Technique*, J. Appl. Phys., vol. 76, No. 7, pp. 4454–4456 (Oct. 1, 1994).

(List continued on next page.)

*Primary Examiner*—Craig E. Church
*Assistant Examiner*—Irakli Kiknadze
(74) *Attorney, Agent, or Firm*—Steven J. Hultquist; Marianne Fuierer; Tristan Fuierer

(57) ABSTRACT

An apparatus and method for mapping film thickness of one or more textured polycrystalline thin films. Multiple sample films of known thickness are provided. Each sample film is irradiated by x-ray at a measurement point to generate a diffraction image that captures a plurality of diffraction arcs. Texture information (i.e., pole densities) of the sample film, is calculated based on incomplete pole figures collected on the diffraction image and used to correct the x-ray diffraction intensities from such sample. The corrected diffraction intensities are integrated for each sample film, and then used for constructing a calibration curve that correlates diffraction intensities with respective known film thickness of the sample films. The film thickness of a textured polycrystalline thin film of unknown thickness can therefore be mapped on such calibration curve, using a corrected and integrated diffraction intensity obtained for such thin film of unknown thickness.

24 Claims, 4 Drawing Sheets

U.S. PATENT DOCUMENTS

I. Tomov, *Secondary Extinction Used in Thickness and Pole Density Measurements of Textured Films by X–Ray Diffraction*, Material Science Forum, vol. 273–275, pp. 145–150 (1998).

Mark Dax, *X–Ray Film Thickness Measurements: Using X–Rays to Measure Film Thickness Permits Additional Information Including Composition, Crystal Structure and Roughness to be Obtained*, Semiconductor International, pp. 91–100 (Aug. 1996).

S.P. Tobin et al., *Composition and Thickness Control and Thin LPE HgCdTe Layers Using X–Ray Diffraction*, Journal of Electronic Materials, vol. 29, No. 6, pp. 781–791 (2000).

H.J. Bunge, Texture Analysis in Materials Science, pp. 46–118 (Butterworths, London, 1982).

Ryong–Joon Roe, *Description of Crystalline Orientation in Polycrystalline Materials.: III General Solution to Pole Figure Inversion*, J. Appl. Phys., vol. 36, No. 6, pp. 2024–2031 (Jun. 1965).

Kurt Lücke et al., *On the Presentation of Orientation Distribution Functions by Model Functions*, Z. Metallkunde, vol. 77, pp. 312–321 (1986).

K. Pawlik et al., *Rolling Texture of Silver Single Crystals Described by the Discrete Orientation Distribution*, ICOTOM 8, pp. 531–536 (ed. J.S. Kallend & G. Gottstein, The Metallurgical Society, 1988).

Daniel Ruer and Raymond Baro, *A New Method for the Determination of the Texture of Materials of Cubic Structure from Incomplete Reflection Pole Figures*, Advances In X–Ray Analysis, vol. 20, pp. 187–200 (1977).

Janos Imhof, *Determiniation of the Oreintation Distribution Function from One Pole Figure*, Textures and Microstrutures, vol. 5, pp. 73–86 (1982).

S. Matthies and G.W. Vinel, *On the Reproducibility of the Orientation Distribution Function of Texture Samples from Pole Figures (Ghost Phenomena)*, Phys. Stat. Sol. (b) 92, K135–K138 (1979).

K. Pawlik, *Determination of the Orientation Distribution Function from Pole Figures in Arbitrarily Defined Cells*, Phys. Stat. Sol. (b) 134, pp. 477–483 (1986).

D. Raabe and K. Lücke, *Analysis of the ADC Method for Direct ODF Calculation by Use of Gauss Models and Standard Functions*, Materials Science Forum, vol. 157–162, pp. 413–418 (1994).

S. Matthies and G.W. Vinel, *On the Reproducibility of the Orientation Distribution Function of Texturized Samples from Reduced Pole Figures Using the Conception of a Conditional Ghost Correction*, Phys. Stat. Sol. (b) 112, K111–K114 (1982).

S. Matthies et al., Standard Distributions in Texture Analysis, vol. 1, pp. 38–45 (Akademie–Verlag, Berlin, 1987).

C.G. Darwin, *The Theory of X–Ray Reflection*, PHIL. MAG., vol. 27, pp. 315–333 (1914).

C.G. Darwin, *The Theory of X–Ray Reflection: Part II*, PHIL. MAG., vol. 27, pp. 675–690 (1914).

C.G. Darwin, *The Reflection of X–Rays from Imperfect Crystals*, PHIL. MAG., vol. 43, pp. 800–829 (1922).

* cited by examiner

METHOD AND APPARATUS FOR THIN FILM THICKNESS MAPPING

FIELD OF THE INVENTION

The present invention generally relates to the field of thin film thickness mapping, and more specifically relates to a method for measuring thickness of textured polycrystalline thin films or coatings.

BACKGROUND OF THE INVENTION

There is a great commercial need for stringent thickness control of crystalline plating, films, and coatings. The performance of many electronic devices is critically dependent on the film thickness. Significant manufacturing cost reductions and improvements in quality and reliability can be achieved by insuring that the applied film thickness is within the acceptance limits for a specific application.

X-ray diffraction (XRD) techniques enable measurement of the thickness of thin films in a non-destructive, non-contact, and quantitative manner.

Conventional XRD-based film thickness measurement analyzes the attenuation of the diffraction intensity, by comparing the integrated intensity of the incident x-ray with the integrated intensity of the x-ray diffracted from the films themselves or from the films and the substrate, according to the kinematical expression of the integrated diffraction intensity.

J. Chaudhuri (J. Chaudhuri and F. Hashmi, "Determination of thickness of multiple layer thin films by and x-ray diffraction technique," *J. Appl. Phys.* 76 (7), (1994), pp. 4454–4456) proposed a technique for determining thickness of multiple heteroepitaxial films deposited on a single crystal substrate, based on the integrated intensity reflected on rocking curve of each film and substrate. Chaudhuri corrects the kinematical expression of the integrated diffraction intensity, by applying the primary and secondary extinction of diffracted x-rays, according to the mosaic crystal model established by C. G. Darwin in *Phil. Mag.*, vol. 27, pp. 315 and 657 (1914) and vol. 43, pg. 800 (1922). The block thickness of such mosaic crystal model was assumed a priori, and the constant referring to block tilts is determined through calibration using a single film with known thickness.

However, the technique disclosed by Chaudhuri applies only to heteroepitaxial films, which are characterized by single crystal-like texture, and is not suitable for determining thickness of a textured polycrystalline film or stacks of films, where the crystallographic texture varies widely and impacts the diffraction intensities differently.

Ruud (C. O. Ruud, M. E. Jackobs, "Method and apparatus for in-process analysis of polycrystalline films and coatings by x-ray diffraction," U.S. Pat. No. 5,414,747, May 9, 1995) proposed to use multiple position sensitive detectors to register multiple diffraction peaks simultaneously. Specifically, Ruud uses the diffraction intensity of one or more diffraction peaks from the substrate to calculate the thickness of the coating, presumably according to the absorption equations. However, Ruud does not suggest or teach elimination of crystallographic texture effects from the measurements of diffraction peak intensity.

It is therefore an object of the present invention to provide a method for determining thickness of textured polycrystalline thin films, by correcting the diffraction intensity measurement to eliminate crystallographic texture impacts therefrom.

It is another object of the present invention to provide a film thickness mapping system, which rapidly and automatically collects and processes diffraction data for determining thickness of textured polycrystalline thin films.

Other objects and advantages will be more fully apparent from the ensuing disclosure and appended claims.

SUMMARY OF THE INVENTION

One aspect of the present invent relates to a method for determining film thickness of a textured polycrystalline thin film of unknown thickness, comprising the steps of:

(a) providing a plurality of sample films comprising textured polycrystalline materials and having known film thickness;

(b) collecting multiple incomplete pole figures of a sample film, by:
  (i) irradiating a measurement point on such sample film with radiation energy from a radiation source;
  (ii) detecting the radiation energy diffracted from such sample film at a detection locus, wherein the detection locus is in sufficient proximity to the measurement point for capturing a plurality of diffraction arcs within a single data capture frame; and
  (iii) generating a diffraction image containing multiple incomplete pole figures;

(c) calculating complete pole densities for a particular set of diffracting planes of such sample film, based on the incomplete pole figures collected on the diffraction image;

(d) obtaining values of diffraction intensities for the particular set of diffracting planes from the diffraction image;

(e) correcting the values of diffraction intensities to eliminate crystallographic texture impacts therefrom, by using the pole densities calculated in step (c);

(f) integrating the corrected values of diffraction intensities for the particular crystallographic orientation to form a corrected and integrated diffraction intensity for the particular set of diffracting planes of such sample film;

(g) repeating steps (b) to (f) for each sample film, while fixing the instrumental set up during data acquisition for all the sample films, so as to obtain a corrected and integrated diffraction intensity of the particular set of diffracting planes for each sample film;

(h) constructing a calibration curve, which correlates the corrected and integrated diffraction intensities in step (g) obtained for the sample films with the respective known film thickness of such sample films;

(i) obtaining a corrected and integrated diffraction intensity for the particular set of diffracting planes of the textured polycrystalline thin film of unknown thickness; and (j) mapping the film thickness of the textured polycrystalline thin film on the calibration curve, based on the corrected and integrated diffraction intensity obtained for such textured polycrystalline thin film.

The phase "thin film" as used herein refers to a film having a thickness within the range of from about 0.1 nm to about 2000 nm.

Another aspect of the present invention relates to a thickness mapping system for determining film thickness of a textured polycrystalline thin film, comprising:

a sample comprising the textured polycrystalline thin film deposited on a generally planar substrate, said sample defining an associated sample plane;

a radiation source for directing radiation energy to a measurement point on the sample;

a 2-dimensional area detector that registers radiation energy diffracted from the sample at the measurement point, with the radiation source and the 2-dimensional area detector being in a fixed spatial relationship to one another and sufficiently proximate to the measurement point to capture a plurality of diffraction arcs within a single data capture frame of the area detector;

a sample motion assembly for translating the sample in the sample plane; and a computer-based film thickness processor, construed and arranged to collect and process diffraction data for determining film thickness of the textured polycrystalline thin film.

BRIEF DESCRIPTION OF THE DRAWINGS

FIG. 6 shows comparative measurement of sheet resistance and XRD thickness measurement of the present invention on a-Ta films deposited on 200 mm single crystal silicon wafers.

DETAILED DESCRIPTION OF THE INVENTION, AND PREFERRED EMBODIMENTS THEREOF

Figure 1:
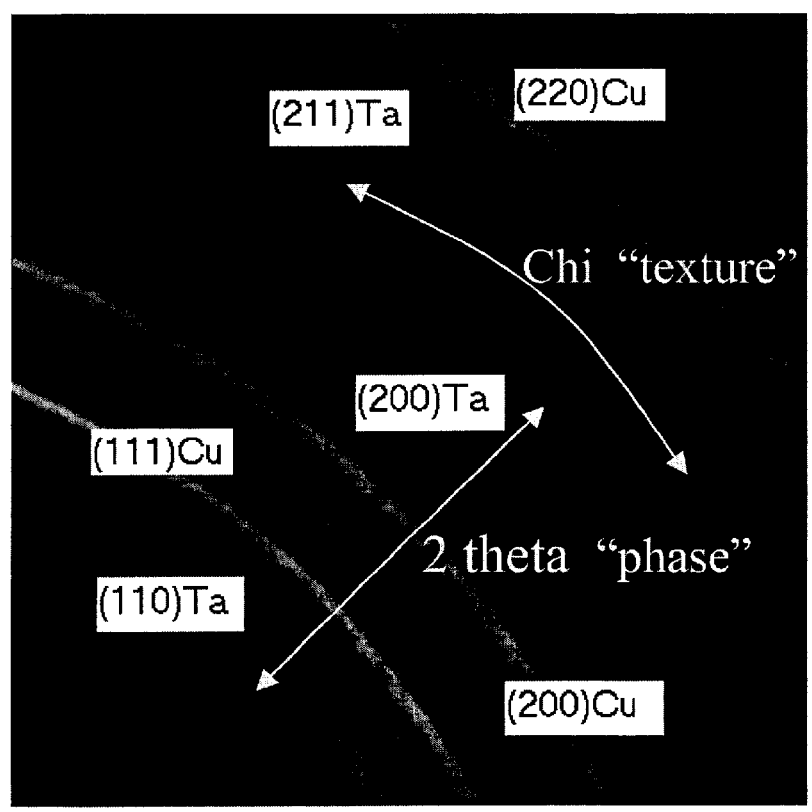
FIG. 1 shows a diffraction image for a Ta/Cu film stack, as captured by a 2-dimensional area detector, which contains multiple Debye rings for several (hkl) reflections of the Ta and Cu films.

U.S. Pat. No. 6,301,330 B1 for "Apparatus and Method for Texture Analysis in Semiconductor Wafers" issued to David S. Kurtz, who is a co-inventor of the present invention, is incorporated hereby by reference in its entirety for all purposes.

In a perfectly random polycrystalline thin film, where there is no significant self-absorption of x-rays (due to the thinness of the film), the total registered diffraction intensity $I_{randomtotal}^{hkl}$ for a particular set of diffraction planes (hkl) is proportional to the irradiated volume V and the data collection time $\Delta t$, according to the following equation:

$$I_{randomtotal}^{hkl} = V \times \Delta t \quad (1)$$

When the irradiated area (i.e., the cross-sectional area of the incident x-ray beam projected on the sample surface) is fixed, the irradiated volume V is a function of the film thickness d and can be expressed as k(d). Therefore, equation (2) can be written into:

$$I_{randomtotal}^{hkl} = k^{hkl}(d) \times \Delta t \quad (2)$$

However, the diffraction intensities detected from a textured polycrystalline thin film differ significantly in comparison with the diffraction intensities of the perfectly random polycrystalline thin film, due to preferred orientation of diffracting crystallites. The relationship between the diffraction intensity of a textured polycrystalline thin film $I_{textured}^{hkl}(\Psi,\Phi)$, as measured for a particular set of diffraction planes (hkl) at a direction defined by polar coordinates $(\Psi,\Phi)$ in the sample coordinate system, and the diffraction intensity of a perfectly random polycrystalline thin film $I_{random}^{hkl}$ is expressed by the following equation:

$$I_{random}^{hkl} = I_{texture}^{hkl}(\Psi,\Phi)/P^{hkl}(\Psi,\Phi) \quad (3)$$

Wherein $P^{hkl}(\Psi,\Phi)$ is the pole density of a particular set of diffraction planes (hkl) at a direction defined by polar coordinates $(\Psi,\Phi)$ in the sample coordinate system, expressed as a volume fraction of:

$$P^{hkl}(\Psi,\Phi) = \frac{dV}{V} \bigg/ \frac{d\Omega}{4\pi} \quad (4)$$

Wherein V is the total irradiated volume, dV is the volume of crystallites having the crystallographic orientation (hkl) within a solid angle element $d\Omega$ from the direction defined by polar coordinates $(\Psi,\Phi D)$.

When the polycrystalline film is perfectly random, its pole density $P_{random}^{hkl}$ equals 1, regardless of the $(\Psi,\Phi)$ orientation. When the polycrystalline film is textured, its pole density $P^{hkl}(\Psi,\Phi)$ can be calculated from the Orientation Distribution Function (ODF), which is the quantitative/mathematical measure of texture, as disclosed by U.S. Pat. No. 6,301,330 B1.

Specifically, U.S. Pat. No. 6,301,330 B1 discloses a method that uses an area x-ray detector, a unique set of sample motions, a particular fixed special geometrical relationship between the x-ray beam source, the area x-ray detector, and the sample measurement point, and a unique and innovative texture analysis protocol for capturing multiple incomplete pole figures within one data capture frame and calculating the ODF from such incomplete pole figures, via pole figure inversion.

The use of area x-ray detector, as opposed to the point scanning detectors traditionally used for detecting diffracted x-ray beams, greatly reduces data acquisition time by capturing x-ray diffraction with a relatively large range in the $2\theta$ direction and $\Psi$ direction. Multiple diffraction arcs (sections of Debye rings) can thus be captured in a single detector frame, so as to reduce data acquisition time and increase accuracy.

The x-ray beam source and the area x-ray detector are also arranged in carefully-chosen fixed spatial relationship (thus fixed ranges of $2\theta$ and $\Psi$) that are optimally integrated with the particular set of sample motions used (only within the sample plane as defined by the planar surface of the sample), which enables the elimination of the Eulerian cradle and the $\theta$–$2\theta$ rotating stages used in the traditional x-ray diffraction system.

U.S. Pat. No. 6,301,330 B1 also provides a texture analysis protocol that simultaneously analyzes the diffraction information from all the diffraction arcs captured within the detector area, which enables fine meshing of the $\Phi$ and $\Psi$ angles, and determination of the ODF value and volumetric fractions of texture components from incomplete pole figures.

The three-dimensional distributions of crystallites (i.e., ODF) in polycrystalline aggregates can be calculated from two-dimensional projections of ODF (i.e., pole figures), by means of direct pole figure inversion or by series expansion methods. The series expansion methods {(H. J. Bunge, Texture Analysis in Materials Science (Butterworths, London, 1982)), (R. J. Roe, "Description of crystalline orientation in polycrystalline materials. (III) General solution to pole figure inversion," *J. Appl Phys*. 36 (1965), 2024–2031)}, and the series expansion method using Gauss-type model functions (K. Lucke, J. Pospiech, and J. Jura, Z. Metallkunde 77 (1986), 312) has intrinsic truncation errors and are not suited for analyzing sharp textures (W. Truszkowski, J. Pospiech, T. Pawlik, "Rolling Texture of Silver Single Crystals Described by the Descrete Orientation Distribution, ICOTOM 8, ed. J. S. Kallend & G. Gottstein, TMS, P 531–536, 1988). The direct methods, including the vector method (D. Ruer and R. Barro, Adv. X-ray Anal. 20 (1977), 187), the Imhof method (J. Imhof, Textures and microstructures, 4 (1982), 189), the Williams-Imhof-Matthies-Vinel (WIMV) method (S. Matthies, "On the reproducibility of the orientation distribution function of texture samples from pole figures (ghost phenomena), Phys. Stat. Sol. (b) 92 (1979), K135–K138), and the Arbitrary Defined Cell (ADC) method (K. Pawlik, Phys. Stat. Sol. (b) 124 (1986), 477) lead to errors caused by the under-determination of the set of linear equations relating discrete cells in pole figures to cells in the three-dimensional orientation space. In the case of sharp textures, the WIMV method and the ADC method work the best (D. Raabe and K. Lucke, "Analysis of the ADC Method for Direct ODF Calculation by Use of Gauss Models and Standard Functions," Materials Science Forum 157–162 (1994) 413–418).

The ODF calculation protocols of U.S. Pat. No. 6,301,330 B1therefore utilize a direct method with an arbitrary step resolution (e.g., 1, 2, 3, and 5 degrees). The direct method is either a modified WIMV method (S. Matthis and G. W. Vinel "On the reproduction of the orientation distribution function of textured samples from reduced pole figures using conceptions of a conditional ghost correction," Phys. Stat. Sol. (b) 112 (1982), K111–120) or an ADC method (K. Pawlik, Phys. Stat. Sol. (b) 124 (1986), 477).

The pole densities $P^{hkl}(\Psi,\Phi)$ are calculated for each (hkl) orientation of interest and for each $(\Psi,\Phi)$ direction by applying an appropriate projection operator to the ODF. (S. Mathis, G. W. Vinel, K. Helming, Standard Distributions in Texture Analysis (Akademie-Verlag, Berlin, 1987))

The values of diffraction intensities for the (hkl) orientation of interest within an integration region i, as finely meshed over small increments of $\Delta\Psi$ and $\Delta 2\theta$ (usually not more than 0.1 degree), are then obtained from the diffraction image captured by the area x-ray detector, as in FIG. 1. An example of the integration region i is shown by the square on the Debye ring originating from the (200) planes of Cu in FIG. 1. The obtained diffraction intensity within integration region i is $\{I_{texture}^{hkl}(\Psi,\Phi)\}_i$.

The discrete values of $P^{hkl}(\Psi,\Phi)$ corresponding the region i, as calculated from the ODF, are then used to correct the discrete values of the diffraction intensities $\{I_{texture}^{hkl}(\Psi,\Phi)\}_i$, according to equation (3), to eliminate the impact of the crystallographic texture from the diffraction intensity. Therefore, the discrete values of diffraction intensities $\{I_{texture}^{hkl}(\Psi,\Phi)\}_i$ collected on the textured sample are converted to equivalent random diffraction intensities $\{I_{random}^{hkl}(\Psi,\Phi)\}_i$ as follows:

$$\{I_{radom}^{hkl}(\Psi,\Phi)\}_i = \{I_{texture}^{hkl}(\Psi,\Phi)\}_i / P^{hkl}(\Psi,\Phi)_i \quad (5)$$

By integrating the values of equivalent random diffraction intensities $\{I_{radom}^{hkl}(\Psi,\Phi)\}_i$ of the (hkl) reflection, total random diffraction intensity $I_{random}^{hkl}$ can be obtained, according to the following equation:

$$I_{randomtotal}^{hkl} = \sum_{i=1}^{i=N} \{I_{random}^{hkl}(\Psi,\Phi)\}_i / N \quad (6)$$

$$N = \{(\Psi_{max} - \Psi_{min})/\Delta\Psi\}\{2\pi/\Delta\Phi\}$$

wherein the summation is carried out on all locations $(\Psi,\Phi)$ of the experimental pole figure (hkl).

Another method of obtaining the integrated intensity which is used for quantitative phase analysis in equation (2) is based upon averaging the registered intensities $\{I_{texture}^{hkl}(\Psi,\Phi)\}_i$ over all orientations in the pole figure space. A correction factor c is calculated as follows:

$$c = \frac{\sum_{\Psi=0}^{\Psi=\pi/4} \sum_{\Phi=0}^{\Phi=2\pi} P_i^{hkl}(\Psi,\Phi)_{calculated}}{\sum_{\Psi=\Psi_{min}}^{\Psi=\Psi_{max}} \sum_{\Phi=0}^{\Phi=2\pi} P_i^{hkl}(\Psi,\Phi)_{calculated}} \quad (7)$$

where $\Psi_{min}$ and $\Psi_{max}$ are the limits of the measured incomplete pole figure, and the $P_i^{hkl}(\Psi,\Phi)_{calcuated}$ are the pole figures re-calculated from the ODF. The corrected integrated intensity (equivalent to a random sample) is calculated as:

$$I_{randomtotal}^{hkl} = c \sum_{\Psi=\Psi_{min}}^{\Psi=\Psi_{max}} \sum_{\Phi=0}^{\Phi=2\pi} \{I_{textured}^{hkl}(\Psi,\Phi)\}_i \quad (8)$$

The correction factor c is used to compensate for the intensity missing from the incomplete experimental pole figures.

The calculation of pole densities can be simplified if the area detector is sufficiently close to the sample measurement point for capturing a whole Debye cone (e.g., in a transmission mode) or a diffraction arc that covers a $\Psi$ range of not less than 90 degrees for a particular (hkl) phase. A series of diffraction images with a whole Debye cone (360 degrees) or diffraction arcs of not less than 90 degrees collected at $\Phi$ angles covering a sufficient range of the $\Phi$ domain is equivalent to measurement of a full pole figure, and the pole densities $P^{hkl}(\Psi,\Phi)$ can be directly calculated by using a normalization equation (9) as follows, without having to calculate such pole densities from ODF:

$$\frac{1}{4\pi} \int_0^\pi \int_0^{2\pi} P^{hkl}(\Psi,\Phi)\sin\Psi \, d\Psi = 1 \quad (9)$$

Moreover, when the textured polycrystalline thin films have fiber texture (i.e, each crystallite or grain has the same particular crystallographic orientation parallel to a particular direction on the sample, for example, the direction normal to the sample surface, and is randomly rotated around this axis), the pole density is independent of the azimuthal polar coordinate $\Phi$ and can be expressed as $P^{hkl}(\Psi)$. The fiber symmetry may be experimentally enforced by spinning the sample during measurements and using equations (5) and (6) or (7) and (8) for obtaining the total random diffraction spectrum.

The relationship between corrected integrated diffraction intensities of textured polycrystalline thin films, as equivalents of diffraction intensities of random samples, and the film thickness of such textured polycrystalline thin films, can then be used for construction of a calibration curve. Such calibration curve is useful for determining the film thickness of a textured polycrystalline thin film of unknown thickness, when a corrected integrated diffraction intensity of a particular crystallographic orientation is determined for such textured polycrystalline thin film of unknown thickness.

During the calibration process, it is preferred that the experimental conditions, such as the x-ray influx, measurement geometry, and x-ray optics, are fixed for all the calibration cycles. The apparatus described in U.S. Pat. No. 6,301,330 provides fixed measurement geometry and x-ray optics. Therefore, during the x-ray diffraction data acquisition, the diffracted x-ray beams originate from the same measurement location on the sample with same irradiated volume. Under such constant measurement conditions, the film thickness measurement can be calibrated, by constructing a calibration curve reflecting a calibration function that is valid for all measurements carried out for a given material under the constant measurement conditions.

A plurality of sample films comprise textured polycrystalline materials are therefore provided, and the film thickness of these sample films is known (i.e., predetermined). The diffraction data of each film is captured on a diffraction image according to the method described hereinabove, and discrete diffraction intensities of a particular (hkl) orientation are correspondingly corrected, using pole densities calculated based on the pole figures captured on the diffraction image, and integrated into an equivalent random total diffraction intensity for the particular (hkl) reflection for each thin film. A calibration curve can then be constructed, which correlates the corrected and integrated diffraction intensities of the particular (hkl) orientation with the respective film thickness of the sample films, according to the following equation:

$$t_n = f_n^{hkl}(I_n^{hkl}/\Delta t) \qquad (10)$$

wherein $t_n$ is the thickness of the n-th thin film that comprises the textured polycrystalline material, $f_n^{hkl}$ is the function describing the calibration relationship for a particular (hkl) reflection, which is valid for all measurements carried out for all the thin films that comprise the textured polycrystalline material of interest, and $I_n^{hkl}/\Delta t$ is the integrated intensity rate of the n-th thin film obtained for the particular (hkl) orientation, after eliminating texture (i.e., corrected).

The corrected and integrated diffraction intensity for each thin film is preferably normalized by the total diffraction intensity registered by the area detector before being used to construct the calibration curve. Thus, each set of data is self-consistent and independent of the variations of the intensity of the initial x-ray beam.

Figure 2:
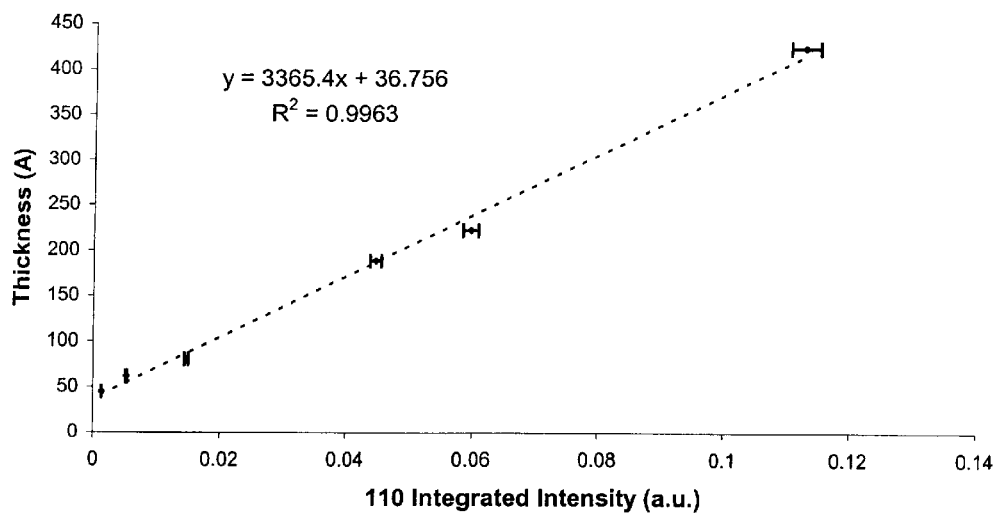
FIG. 2 shows a calibration curve constructed for the (110) crystallographic orientation of Ta, which correlates the normalized, corrected, and integrated diffraction intensities of the (110) phase with film thickness of Ta films.

FIG. 2 shows a calibration curve constructed for the diffraction intensities of (110) orientation of α-Ta film. A 1% error in the integrated intensity translates to 2 Å uncertainty in thickness calculations.

The method described herein can be used to determine the thickness of a single film sample, or the thickness of each film layer in a film stack that comprises multiple film layers. The present invention is particularly suitable for determining thickness of films contained in a multi-film stack, because diffraction data of the multiple films in the film stack can be simultaneously captured by an area detector within a single diffraction image, and can be used to determine thickness of each film. The thickness of the top layer film is determined first and it is subsequently used for absorption correction applied to diffraction cones originating from the film underneath. In such a way the diffraction intensity for a particular film in a stack is corrected for absorption of x-rays in the film deposited on top of this particular film.

Figure 3:
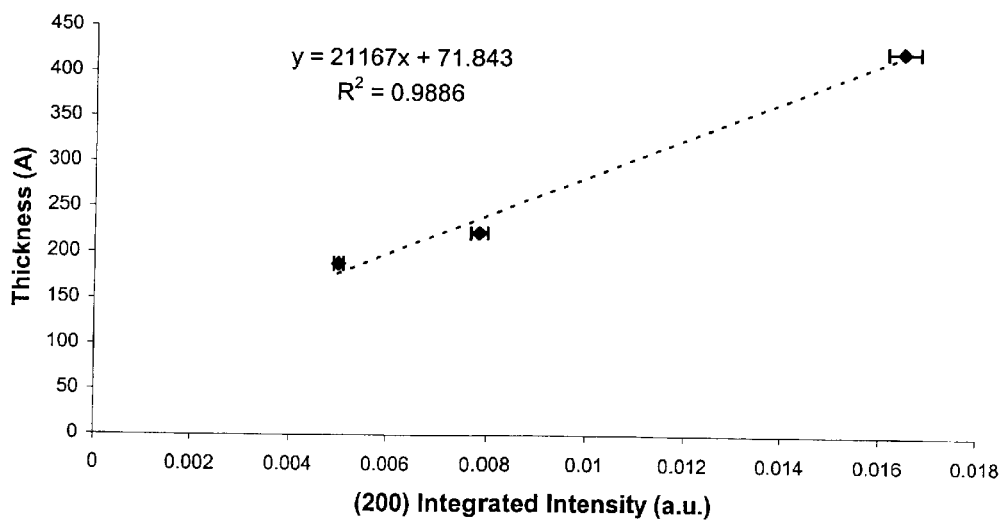
FIG. 3 shows a calibration curve constructed for the (200) crystallographic orientation of Ta, which correlates the normalized, corrected, and integrated diffraction intensities of the (200) phase with film thickness of Ta films.
Figure 4:
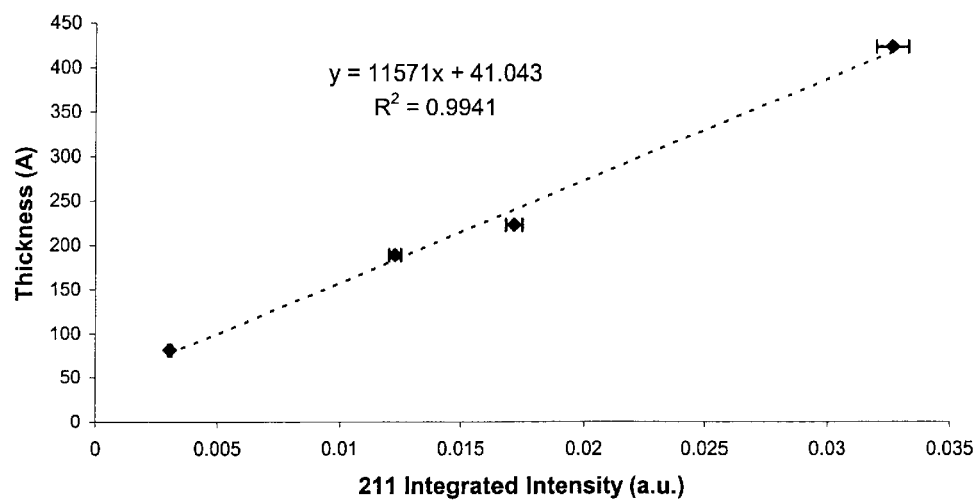
FIG. 4 shows a calibration curve constructed for the (211) crystallographic orientation of Ta, which correlates the normalized, corrected, and integrated diffraction intensities of the (211) phase with film thickness of Ta films.

As described hereinabove, a single diffraction image captured by an area detector typically contains multiple diffraction arcs for multiple (hkl) set of planes for a given material. For example, the diffraction image of FIG. 1 contains three (hkl) reflections for the Ta film, namely the (110)Ta, (200)Ta, and (211)Ta reflections, and three (hkl) reflections for the Cu film, namely the (111)Cu, (200)Cu, and (220)Cu reflections. In one embodiment of the present invention, multiple calibration curves are constructed for the given material, according to the calibration method described hereinabove, while each calibration curve corresponds to one particular crystallographic set of planes (hkl) of the material of interest. For example, FIGS. 3 and 4 show the additional calibration curves constructed for the diffraction intensities of the (200)Ta and (211)Ta reflections. All the calibration curves constructed for a given material can be subsequently used for thickness measurement of a thin film of unknown thickness, by averaging all the thickness values determined using the multiple calibration curves, so as to provide for higher reliability and precision through use of multiple data sets simultaneously.

The calibration curves can be used in two different ways:
(a) In the case of a single-phase film the calibration curves are used to assess the thickness of the film, directly from equation (10);
(b) In the case of a multi-film stack, the calibration curves can used to determine the thickness of each film layer, based on the corrected and integrated diffraction intensity calculated for each film layer. Because the 2-dimensional area detector of the present invention is capable of concurrently capturing multiple incomplete pole figures for each textured polycrystalline thin film of a multi-film stack within one diffraction image, the corrected and integrated diffraction intensities of all film layers can be determined using one diffraction image, which can then be correlated to respective thickness of respective film layers, by using the calibration curves.

In the present invention, absorption corrections are applied to the diffraction data when necessary, but in most cases where the thickness of the film ranges from tens to hundreds of Angstroms, the adsorption correction is insignificant and is therefore unnecessary.

A further aspect of the present invention relates to a thickness mapping system, comprising:
   a sample comprising the textured polycrystalline thin film deposited on a generally planar substrate, said sample defining an associated sample plane;
   a radiation source for directing radiation energy to a measurement point on the sample;
   a 2-dimensional area detector that registers radiation energy diffracted from the sample at the measurement point, with the radiation source and the 2-dimensional area detector being in a fixed spatial relationship to one another and sufficiently proximate to the measurement point to capture a plurality of diffraction arcs within a single data capture frame of the area detector;
   a sample motion assembly for translating the sample in the sample plane; and
   a computer-based film thickness processor, construed and arranged to collect and process diffraction data for determining film thickness of the textured polycrystalline thin film.

The thickness mapping system of the present invention significantly reduces the data acquisition time required, by employing a collimated source of monochromatic radiation, for directing radiation energy to a measurement point on a sample, and a 2-dimensional area detector for registering radiation energy diffracted from the measurement point, with the collimated source of radiation energy and the 2-dimensional area detector being in a fixed spatial relationship to each other and sufficiently proximate to the sample measuring point to capture a plurality of diffraction arcs within a single data capture frame of the detector.

The use of an area x-ray detector, as opposed to the point scanning detectors traditionally used for detecting diffracted x-ray beams, greatly reduces data acquisition time by capturing a relatively large range of reciprocal space, and storing it as a digitized electronic file. Multiple diffraction arcs can thus be captured in a single detector frame, both reducing data acquisition time and increasing accuracy.

The x-ray beam source and area x-ray detector of the present invention are arranged in carefully chosen fixed spatial locations, which determine correspondingly fixed ranges of sample coverage in $2\theta$ and $\Psi$ directions. Conventional x-ray diffraction systems require movement of the detector in the $2\theta$ direction and movement of the sample in the $\Psi$ direction in order to obtain a sufficiently large number of diffraction spots for purpose of analyzing grain size. In contrast, the present invention, by fixing the spatial relationship between the x-ray beam source and area x-ray detector, fixes the sample coverage in $2\theta$ and $\Psi$ directions and thus eliminates motion of the detector and sample in these two directions.

Moreover, such fixed spatial locations between the x-ray beam source and area x-ray detector are optimally integrated with a particular set of sample motions (usually planar motion within the sample plane defined by the sample holding device in order to obtain suitable texture information required for the thickness measurement), and optimally integrated with a primary set of materials that the inventive system is used to analyze. This enables the elimination of the conventional Eulerian cradle used to rotate the sample in the $\Psi$ direction, the $\theta$ rotating stage used to rotate the sample, and the $2\theta$ rotating stage used to rotate the detector, as required in the prior art systems to obtain texture information. Elimination of these motion stages greatly simplifies the system and significantly reduces its cost.

Figure 5:
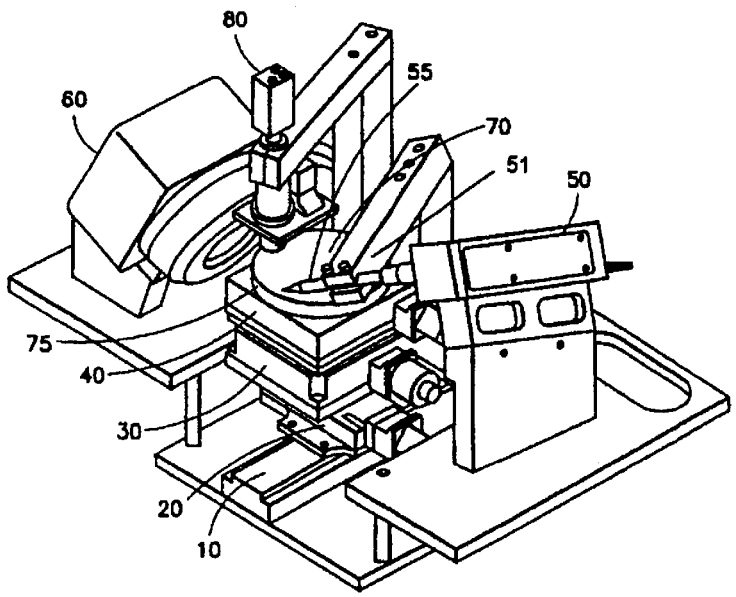
FIG. 5 shows a perspective depiction of the essential components of the apparatus of the present invention applied to the analysis of semiconductor wafers, and of their spatial arrangement.

An example of the apparatus used in the present invention is shown in FIG. 5. The apparatus of the present invention utilizes an x-ray source with collimation device and an area x-ray detector with its positioning optimized for a particular range of coverage within reciprocal space.

The apparatus preferably comprises three interacting components: the collimated x-ray source components, the sample handling apparatus, and the area detector. The x-ray area detector 60 is mounted to a rigid base. Also mounted to the rigid base are the sealed x-ray source 50, monochromator 51, and x-ray collimator 55. In this particular example, the sample handling apparatus consists of a sample motion apparatus, having a y-stage 10, an x-stage 20, a z-stage 30, and a $\phi$-stage 40. Also shown is an optional video microscope 80. The example application of the invention is primarily designed to handle sample 70 of about 300 millimeters in diameter, but the apparatus can be readily modified to handle larger or smaller samples.

A preferred aspect of the invention is that it fixes the x-ray source and detector in specific spatial locations. The sample handling apparatus is mounted in such a way to not spatially interfere with the x-ray source, collimator or detector, but allow sample motion sufficient to cover all locations of the sample surface, and to also allow in-plane rotation at all of these locations. In the example configuration, the sample motion stages are arranged in the following order from top to bottom: $\phi$ rotation, z (vertical) motion, x linear motion, and y linear motion. These sample motions are configured in such a way as to allow full sample motion, as well as close proximity of the area detector to the wafer measure point 75.

In one example, the sample motion-effecting means effectuates planar motions—movements in the plane of the sample. The sample can be in the form of a thin wafer or other planar structure, defining a corresponding sample plane. The movements of the sample for the analysis are in this sample plane, and the sample is not rotated out of the sample plane for data acquisition; rather, all sample movements are "in-plane" movements, as effected by the sample motion assembly.

In a more complex example, the sample is not planar, and the sample motion-effecting means effectuates non-planar motions in order to keep the measuring point in a constant plane.

In the present invention as applied to semiconductor wafer analysis, the fixed ranges of $2\theta$ and $\Psi$ are optimized for a group of specific material systems, by placing the detector 60 and x-ray source 50 at very specific permanent locations. By capturing a desired set of crystallographic reflections over a preferred range of $\Psi$ for each reflection, the maximum amount of texture information can be extracted from the measurement process through a new and more efficient analysis.

A Hi-Star® multiwire gas proportional counter, produced by Bruker AXS, Madison, Wis., is currently a preferred area x-ray detector suitable for diffraction data acquisition in polycrystalline materials. It offers high sensitivity combined with a large total circular detection area that is 11.5 centimeters in diameter. Any other suitable two-dimensional type area detector with sufficient angular range and spatial resolution can be employed, including, but not limited to, x-ray image charge-coupled device (CCD) cameras, x-ray image plates, and other 2-D x-ray detectors. Preferably, such area detector has large area, high sensitivity, and a mechanism for rapid transfer of data to electronic digital format.

The x-ray source can be a standard sealed beam tube, a rotating anode, an integrated sealed tube with a polycapilary optics system, an integrated sealed tube with a grated mirror system or any other suitable source for generating and collimating x-rays.

Additional information concerning the apparatus arrangement is contained in U.S. Pat. No. 6,301,330 for "Apparatus and Method for Texture Analysis on Semiconductor Wafers" issued on Oct. 9, 2001, the contents of which are herein incorporated by reference in their entireties for all purposes.

The film thickness determination is performed by a computer-based film thickness processor, which may comprise a computer, central processor unit (CPU), microprocessor, integrated circuitry, operated and arranged to collect and process diffraction data for determining film thickness of textured polycrystalline thin film, according to the method described hereinabove. Such film thickness processor preferably comprises a film thickness determination protocol for computationally carrying out the thickness determination method described hereinabove. The film thickness determination protocol can be embodied in any suitable form, such as software operable in a general-purpose programmable digital computer. Alternatively, the protocol may be hard-wired in circuitry of a microelectronic computational module, embodied as firmware, or available on-line as an operational applet at an Internet site for film determination.

COMPARATIVE EXAMPLE

Figure 6A:
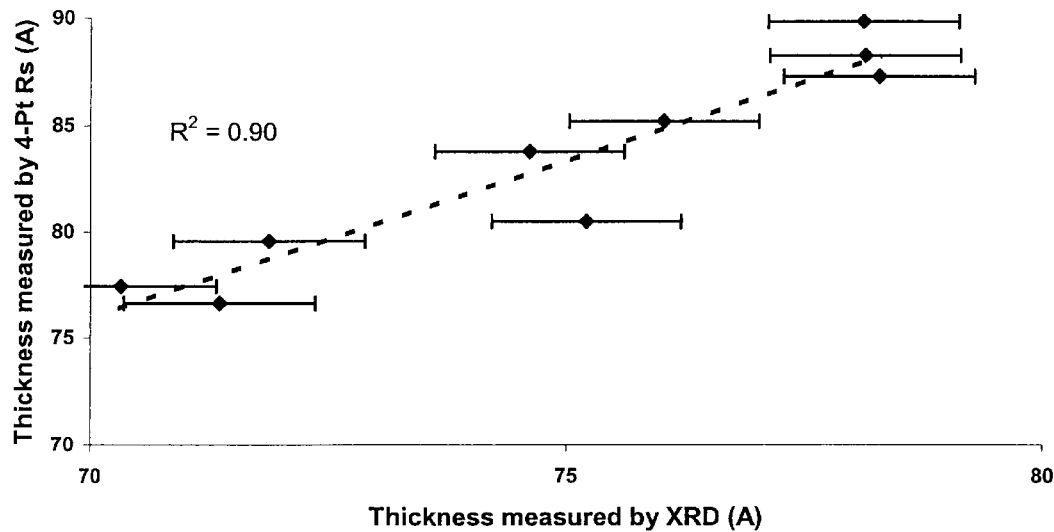
FIG. 6a shows sheet resistance measurement data as converted to film thickness.
Figure 6B:
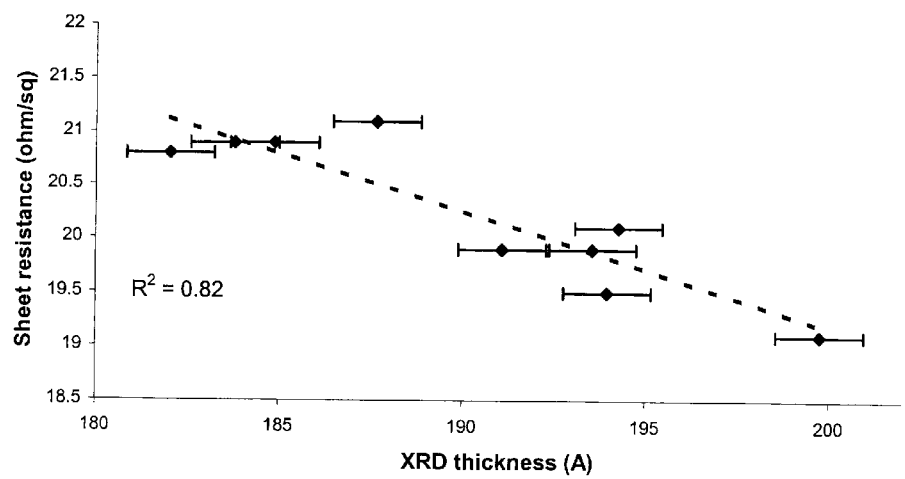
FIG. 6b shows raw sheet resistance data.

In order to verify the accuracy of thickness measurement, comparative measurements were done by means of four-probe sheet resistance measurement, which is a commonly used method for measuring thickness of metallic films. The measurements were carried out on 9 points on 200 mm wafers with sputtered α-Ta films. The results are presented in FIG. 6 for films approximately 70 and 200 Å in thickness.

Although the invention has been variously disclosed herein with reference to illustrative embodiments and features, it will be appreciated that the embodiments and features described hereinabove are not intended to limit the invention, and that other variations, modifications and alternative embodiments will readily suggest themselves to those of ordinary skill in the art. The invention therefore is to be broadly construed, as including such variations, modifications and alternative embodiments, within the spirit and scope of the ensuing claims.

What is claimed is:

1. A method for determining film thickness of a textured polycrystalline thin film of unknown thickness, comprising the steps of:
   (a) providing a plurality of sample films comprising textured polycrystalline materials and having known film thickness;
   (b) collecting multiple incomplete pole figures of a sample film, by:
      (i) irradiating a measurement point on said sample film with radiation energy from a radiation source;
      (ii) detecting the radiation energy diffracted from said sample film at a detection locus, wherein the detection locus is in sufficient proximity to the measurement point for capturing a plurality of diffraction arcs within a single data capture frame; and
      (iii) generating a diffraction image containing multiple incomplete pole figures;
   (c) calculating complete pole densities for a particular set of diffracting planes of said sample film, based on the incomplete pole figures collected on the diffraction image;
   (d) obtaining values of diffraction intensities for the particular set of diffracting planes from said diffraction image;
   (e) correcting the values of diffraction intensities to eliminate crystallographic texture impacts therefrom, by using the pole densities calculated in step (c);
   (f) integrating the corrected values of diffraction intensities for the particular set of diffracting planes to form a corrected and integrated diffraction intensity for the particular set of diffracting planes of said sample film;
   (g) repeating steps (b) to (f) for each sample film, while fixing the instrumental set up during data acquisition for all the sample films, so as to obtain a corrected and integrated diffraction intensity of the particular set of diffracting planes for each sample film;
   (h) constructing a calibration curve, which correlates the corrected and integrated diffraction intensities in step (g) obtained for the sample films with the respective known film thickness of said sample films;
   (i) obtaining a corrected and integrated diffraction intensity for the particular set of diffracting planes of the textured polycrystalline thin film of unknown thickness; and
   (j) mapping the film thickness of the textured polycrystalline thin film on the calibration curve, based on the corrected and integrated diffraction intensity obtained for such textured polycrystalline thin film.

2. The method of claim 1, wherein the complete pole densities for a particular crystallographic orientation in step (c) are calculated by the steps comprising:
   (i) calculating Orientation Distribution Function (ODF) based on the multiple incomplete pole figures collected by step (b); and
   (ii) calculating the complete pole densities for a particular crystallographic orientation from the Orientation Distribution Function.

3. The method of claim 2, wherein the Orientation Distribution Function in step (i) is calculated by using a direct method with an arbitrary step resolution.

4. The method of claim 3, wherein the direct method is selected from the group consisting of the Williams-Imhof-Matthies-Vinel (WIMV) method and the Arbitrary Defined Cell (ADC) method.

5. The method of claim 3, wherein the arbitrary step resolution is not more than 5 degrees.

6. The method of claim 3, wherein the arbitrary step resolution is not more than 1 degree.

7. The method of claim 1, wherein in step (b)(ii), said detection locus is in sufficient proximity to said measurement point for capturing at least one diffraction arc of not less than 90 degrees, and wherein the complete pole density in step (c) is directly calculated for a particular crystallographic orientation reflected by said at least one diffraction arc, by using a normalization equation.

8. The method of claim 7, wherein said detection locus is in sufficient proximity to said measurement point for capturing at least one diffraction arc of about 360 degrees.

9. The method of claim 1, wherein in step (b)(ii), the detection locus is in fixed spatial relationship to the radiation source.

10. The method of claim 9, wherein in step (b)(ii), the polycrystalline thin film is moved only in a sample plane for data acquisition, wherein said sample plane is defined by a planar substrate upon which the polycrystalline thin film is deposited.

11. The method of claim 1, wherein multiple calibration curves are constructed by repeating steps (b)–(h) as in claim 1, each calibration curve corresponding to one particular set of diffracting planes of the textured polycrystalline material.

12. The method of claim 11, wherein said multiple calibration curves are all used for determining the film thickness of a textured polycrystalline thin film of unknown thickness, by averaging multiple values of the film thickness as determined using the multiple calibration curves.

13. The method of claim 1, wherein:
   (1) multiple textured polycrystalline thin films are deposited on a substrate;
   (2) a diffraction image that concurrently contains multiple incomplete pole figures for each textured polycrystalline thin film is generated, which is used to determine a corrected and integrated diffraction intensity of a particular set of diffracting planes for each thin film; and
   (3) thickness of each textured polycrystalline thin film is mapped on the calibration curve, based on the corrected and integrated diffraction intensity determined for each thin film.

14. A thickness mapping system for determining film thickness of a textured polycrystalline thin film, comprising:

- a textured polycrystalline thin film deposited on a generally planar substrate, said sample defining an associated sample plane;
- a radiation source for directing radiation energy to a measurement point on the sample;
- a 2-dimensional area detector that registers radiation energy diffracted from the sample at the measurement point, wherein the radiation source and the 2-dimensional area detector are arranged in a fixed spatial relationship to one another and sufficiently proximate to the measurement point to capture a plurality of diffraction arcs within a single data capture frame of the area detector, so as to generate a diffraction image containing multiple incomplete pole figures;
- a sample motion assembly for translating the sample in the sample plane; and
- a computer-based film thickness processor, construed and arranged to collect and process diffraction data for determining film thickness of the textured polycrystalline thin film, wherein said computer-based film thickness processor comprises computational means for:
  - (a) calculating complete pole densities for a particular crystallographic orientation of said polycrystalline thin film, based on the multiple incomplete pole figures collected on the diffraction image;
  - (b) obtaining values of diffraction intensities for the particular crystallographic orientation from the diffraction image;
  - (c) correcting said values of diffraction intensities to eliminate crystallographic texture therefrom, by using the pole densities calculated in step (a);
  - (d) integrating the corrected values of diffraction intensities for the particular crystallographic orientation; and
  - (e) mapping the thickness of the polycrystalline thin film, based on the corrected and integrated diffraction intensity obtained for such polycrystalline thin film and a calibration curve stored in memory of said computer-based film thickness processor, wherein said calibration curve correlates corrected and integrated diffraction intensities of sample polycrystalline thin films of known thickness with their respective thickness.

15. The thickness mapping system of claim 14, wherein the pole densities for a particular crystallographic orientation are calculated by the steps comprising:
  (i) calculating Orientation Distribution Function (ODF) based on the multiple pole figures on the diffraction image generated by the 2-dimensional area detector; and
  (ii) calculating the pole densities for a particular crystallographic orientation from the Orientation Distribution Function.

16. The thickness mapping system of claim 15, wherein the Orientation Distribution Function is calculated by using a direct method with an arbitrary step resolution.

17. The thickness mapping system of claim 16, wherein the direct method is selected from the group consisting of the Williams-Imhof-Matthies-Vinel (WIMV) method and the Arbitrary Defined Cell (ADC) method.

18. The thickness mapping system of claim 16, wherein the arbitrary step resolution is not more than 5 degrees.

19. The thickness mapping system of claim 16, wherein the arbitrary step resolution is not more than 1 degree.

20. The thickness mapping system of claim 14, wherein the 2-dimensional area detector is sufficiently proximate to the measurement point for capturing at least one diffraction arc of not less than 90 degrees, and wherein the computer-based film thickness processor directly calculates the pole densities for a particular crystallographic orientation reflected by said at least one diffraction arc, using a normalization equation.

21. The thickness mapping system of claim 20, wherein the 2-dimensional area detector is sufficiently proximate to the measurement point for capturing at least one diffraction arc of about 360 degrees.

22. The thickness mapping system of claim 14, wherein multiple calibration curves are stored in memory of said computer-based film thickness processor, each calibration curve corresponding to one particular set of diffracting planes of the textured polycrystalline material.

23. The thickness mapping system of claim 22, wherein said multiple calibration curves are all used for determining the film thickness of a textured polycrystalline thin film of unknown thickness, by averaging all values of film thickness determined from the multiple calibration curves.

24. The thickness mapping system of claim 14, used for determining thickness of multiple textured polycrystalline thin films deposited on one substrate.

* * * * *

UNITED STATES PATENT AND TRADEMARK OFFICE
CERTIFICATE OF CORRECTION

PATENT NO. : 6,792,075 B2 Page 1 of 1
DATED : September 14, 2004
INVENTOR(S) : Kozaczek et al.

It is certified that error appears in the above-identified patent and that said Letters Patent is hereby corrected as shown below:

Column 4,
Line 26, "($\Psi,\Phi D$)." should be -- ($\Psi,\Phi$). --

Signed and Sealed this

Eleventh Day of January, 2005

JON W. DUDAS
*Director of the United States Patent and Trademark Office*

UNITED STATES PATENT AND TRADEMARK OFFICE
CERTIFICATE OF CORRECTION

PATENT NO. : 6,792,075 B2
APPLICATION NO. : 10/225534
DATED : September 14, 2004
INVENTOR(S) : Kryzysztof J. Kozaczek et al.

It is certified that error appears in the above-identified patent and that said Letters Patent is hereby corrected as shown below:

On the title page

Item (73) Assignee: HyperNex, Inc., State College, PA (US), and
International Business Machines Corp., Hopewell Junction, NY (US)

Signed and Sealed this

Twenty-fourth Day of July, 2007

JON W. DUDAS
*Director of the United States Patent and Trademark Office*